(12) United States Patent
Muser et al.

(10) Patent No.: US 10,682,100 B2
(45) Date of Patent: Jun. 16, 2020

(54) MEASUREMENT SYSTEM AND METHOD FOR MEASURING PARAMETERS IN A BODY TISSUE

(71) Applicant: Luciole Medical AG, Zurich (CH)

(72) Inventors: Markus Hugo Muser, Waedenswil (CH); Juerg Hans Froehlich, Zurich (CH); Dirk Baumann, Zurich (CH)

(73) Assignee: Luciole Medical AG, Zurich (CH)

( * ) Notice: Subject to any disclaimer, the term of this patent is extended or adjusted under 35 U.S.C. 154(b) by 997 days.

(21) Appl. No.: 14/888,862

(22) PCT Filed: May 21, 2014

(86) PCT No.: PCT/EP2014/060414
§ 371 (c)(1),
(2) Date: Nov. 3, 2015

(87) PCT Pub. No.: WO2014/187849
PCT Pub. Date: Nov. 27, 2014

(65) Prior Publication Data
US 2016/0058395 A1    Mar. 3, 2016

(30) Foreign Application Priority Data
May 22, 2013  (CH) .................................... 00997/13

(51) Int. Cl.
*A61B 5/00*    (2006.01)
*A61B 5/145*    (2006.01)
(Continued)

(52) U.S. Cl.
CPC .......... *A61B 5/7278* (2013.01); *A61B 5/0075* (2013.01); *A61B 5/03* (2013.01);
(Continued)

(58) Field of Classification Search
CPC ....... A61B 5/7278; A61B 5/0075; A61B 5/03; A61B 5/031; A61B 5/14546;
(Continued)

(56) References Cited

U.S. PATENT DOCUMENTS 4,204,547 A  *  5/1980  Allocca  .................  A61B 5/022
                                                    600/561
4,730,622 A        3/1988  Cohen
(Continued)

FOREIGN PATENT DOCUMENTS

EP    0481612 A1    4/1992
EP    0933061 B1    10/2004
(Continued)

OTHER PUBLICATIONS

Cyzonyka et al, "Monitoring and Interpretation of Intracranial Pressure", J Neurol Neurosurg Psychiatry, 2004; 75: pp. 813-821.*
(Continued)

*Primary Examiner* — Eric F Winakur
(74) *Attorney, Agent, or Firm* — Alston & Bird LLP

(57) ABSTRACT

A measurement system and method for measuring at least one parameter in a body tissue comprise at least one measurement device to be applied to the body, an optical unit for emitting light waves, wherein at least one wavelength of the light waves lies in the region of the absorption of a body parameter, at least one light guide between the optical unit and the measurement device in order to transmit light waves, and an evaluation unit for evaluating measurement waves. Light waves emitted by the optical unit can be beamed into an optical measurement volume in the body tissue by means of the measurement device, and measurement waves received by the measurement device from the measurement volume can be transmitted from the body tissue to the evaluation unit. The evaluation unit comprises a transfor-
(Continued)

mation algorithm, which transforms pulsatility of a body parameter measured in the measurement volume into a parameter of the pressure in the body tissue, wherein the body parameter is measured by determining the absorption of the light waves.

17 Claims, 2 Drawing Sheets

(51) Int. Cl.
    *A61B 5/03*     (2006.01)
    *A61B 5/1455*     (2006.01)
    *G01N 21/31*     (2006.01)
    *A61B 90/30*     (2016.01)

(52) U.S. Cl.
    CPC .......... *A61B 5/031* (2013.01); *A61B 5/14546* (2013.01); *A61B 5/14552* (2013.01); *A61B 5/14553* (2013.01); *A61B 5/14556* (2013.01); *A61B 5/4519* (2013.01); *G01N 21/314* (2013.01); *A61B 5/6833* (2013.01); *A61B 2090/306* (2016.02); *A61B 2562/0238* (2013.01); *G01N 2021/3129* (2013.01); *G01N 2021/3148* (2013.01)

(58) Field of Classification Search
    CPC ............ A61B 5/14552; A61B 5/14553; A61B 5/14556; A61B 5/4519; A61B 5/6833; A61B 2019/5206; A61B 2562/0238; G01N 21/314; G01N 2021/3129; G01N 2021/3148
    See application file for complete search history.

(56) References Cited

U.S. PATENT DOCUMENTS

| | | | |
|---|---|---|---|
| 4,986,671 A | 1/1991 | Sun et al. | |
| 5,090,410 A | 2/1992 | Saper et al. | |
| 5,579,774 A | 12/1996 | Miller et al. | |
| 5,706,821 A * | 1/1998 | Matcher ............ | A61B 5/14553 250/330 |
| 5,879,373 A | 3/1999 | Roeper et al. | |
| 6,029,671 A | 2/2000 | Stevens et al. | |
| 6,195,574 B1 | 2/2001 | Kumar et al. | |
| 6,261,226 B1 | 7/2001 | McKenna et al. | |
| 6,315,712 B1 | 11/2001 | Rovegno | |
| 6,373,567 B1 | 4/2002 | Wise et al. | |
| 6,390,989 B1 * | 5/2002 | Denninghoff ............ | A61B 3/16 600/561 |
| 6,447,527 B1 | 9/2002 | Thompson et al. | |
| 6,608,684 B1 | 8/2003 | Gelikonov et al. | |
| 7,047,054 B2 | 5/2006 | Benni | |
| 8,190,229 B2 | 5/2012 | Lowery et al. | |
| 8,277,385 B2 * | 10/2012 | Berka ................ | A61B 5/02433 600/485 |
| 2001/0002250 A1 | 5/2001 | Burbank et al. | |
| 2001/0038063 A1 | 11/2001 | Mitsuoka et al. | |
| 2002/0095087 A1 | 7/2002 | Mourad et al. | |
| 2003/0032915 A1 | 2/2003 | Saul | |
| 2003/0071988 A1 | 4/2003 | Smith et al. | |
| 2004/0019293 A1 | 1/2004 | Schweitzer et al. | |
| 2004/0199063 A1 | 10/2004 | O'Neil et al. | |
| 2005/0043596 A1 | 2/2005 | Chance | |
| 2005/0165303 A1 | 7/2005 | Keen et al. | |
| 2007/0019916 A1 | 1/2007 | Takami | |
| 2007/0167867 A1 | 7/2007 | Wolf | |
| 2008/0077023 A1 * | 3/2008 | Campbell ............ | A61B 5/0205 600/502 |
| 2008/0143822 A1 | 6/2008 | Wang et al. | |
| 2008/0208011 A1 | 8/2008 | Shuler | |
| 2010/0292549 A1 * | 11/2010 | Shuler .................. | A61B 5/0215 600/324 |
| 2011/0201962 A1 * | 8/2011 | Grudic .................. | A61B 5/021 600/561 |
| 2012/0071742 A1 | 3/2012 | Medina et al. | |
| 2012/0136240 A1 | 5/2012 | Pranevicius et al. | |
| 2015/0282762 A1 | 10/2015 | Lechot et al. | |

FOREIGN PATENT DOCUMENTS

| | | |
|---|---|---|
| EP | 1301119 B1 | 6/2005 |
| EP | 2294973 A2 | 3/2011 |
| JP | H07-294519 A | 11/1995 |
| JP | 2002-010986 A | 1/2002 |
| JP | 2002-509453 A | 3/2002 |
| JP | 2008-067914 A | 3/2008 |
| JP | 2008-279274 A | 11/2008 |
| JP | 2010-520773 A | 6/2010 |
| WO | WO 1994/027494 A1 | 12/1994 |
| WO | WO 1998/08434 A1 | 3/1998 |
| WO | WO 1999/037204 A1 | 7/1999 |
| WO | WO 2001/040776 A1 | 6/2001 |
| WO | WO 2005/082225 A1 | 9/2005 |
| WO | WO 2007/064984 A2 | 6/2007 |
| WO | WO 2007/132868 A1 | 11/2007 |
| WO | WO 2009/062189 A1 | 5/2009 |
| WO | WO 2010/015094 A2 | 2/2010 |

OTHER PUBLICATIONS

Fantini et al., Figure—Absorption Spectra of Hemoglobin and Water at 300-1500nm, Handbook of Optical Biomedical Diagnostics, ed. Tuchin, SPIE Press, Ch 7, pp. 405-453, 2002 (Year: 2002).*
Japan Patent Office, Search Report for Application No. 2016-514389, dated Dec. 5, 2016, 18 pages, Japan.
Di Ieva, Antonio, et al., "Analysis of Intracranial Pressure Past, Present, and Future", *The Neuroscientist*, Feb. 6, 2013, pp. 592-603, vol. 19, Issue 6, SAGE Publications Inc, U.S.A.
Fan, J.Y., et al., "Intracranial Pressure Waveform Morphology and Intracranial Adaptive Capacity", *American Journal of Critical Care*, Nov. 2008; pp. 545-554, vol. 17, No. 6., The American Association of Critical-Care Nurses, U.S.A.
International Searching Authority, International Search Report for International Application No. PCT/EP2014/060414, Aug. 18, 2014, 7 pages, European Patent Office, The Netherland.
Raksin, Patricia B., et al., "Noninvasive Intracranial Compliance and Pressure Based on Dynamic Magnetic Resonance Imaging of Blood Flow and Cerebrospinal Fluid Flow", *Neurosurg Focus*, 2003, 13 pages, vol. 14, No. 4, retrieved from <http://www.medscape.com/viewarticle/452769_print> on Oct. 30, 2015.
Swiss patent application of the applicant entitled "Messvorrichtung zur Bestimmung zerebraler Parameter" (Measuring Device for Determining Cerebral Parameters), No. 02266/12 of Nov. 6, 2012. (This corresponds to US 2015-0282762 A1 referenced above.
Themelis, George, et al. "Near-Infrared Spectroscopy Measurement of the Pulsatile Component of Cerebral Blood Flow and Volume from Arterial Oscillations", *Journal of Biomedical Optics*, Jan. 2007, pp. 014033-1 to -7, vol. 12, Issue 1, International Society for Optics and Photonics, U.S.A.

* cited by examiner

MEASUREMENT SYSTEM AND METHOD FOR MEASURING PARAMETERS IN A BODY TISSUE

CROSS REFERENCE TO RELATED APPLICATIONS

This application is a national stage application, filed under 35 U.S.C. § 371, of International Application No. PCT/EP2014/060414, filed May 21, 2014, which claims priority to Swiss Application No. 00997/13, filed May 22, 2013, the contents of both of which as are hereby incorporated by reference in their entirety.

BACKGROUND

Technical Field

This invention relates to a measurement system and a method for measuring parameters of a body tissue, such as the determination of blood volume and blood flow in the brain and the muscles or the measurement of the intracranial pressure. In particular the invention relates to a non-invasive measurement of cerebral and muscular parameters.

Related Art

The content of the cranium is composed of the non-compressible components brain, cerebral blood volume (CBV) and cerebrospinal fluid (liquor cerebrospinalis; CSF). After exhaustion of the intracranial compensation mechanisms, such as e.g. reduction of the cerebrospinal fluid production, decrease of the CBV, processes requiring space lead to an increase in intracranial pressure. These circumstances follow e.g. from the Monroe-Kellie doctrine. With increase of the intracranial pressure (ICP) over 50 mmHg, the cerebral perfusion pressure (CPP) can no longer be maintained, and additional damage to brain areas results through a global brain ischemia, such as e.g. is known from "Analysis of Intracranial Pressure: Past, Present and Future", A. Di Ieva et al; *The Neuroscientist;* 6 Feb. 2013. The CPP is thereby identified as the difference between the mean arterial pressure and the ICP. Understood by intracranial pressure, ICP, is by definition the supratentorial cerebrospinal fluid pressure, i.e. the pressure in the lateral ventricles and in the subarachnoid space over the cerebral convexity. According to the conventional view, ICP rises are due to a swelling of the brain, e.g. in the case of a defective blood-cerebral barrier, or a cytotoxic cerebral edema, such as an intracellular water accumulation, an additional space requirement, e.g. through tumor, hemorrhage, etc., or a cerebrospinal fluid, circulatory or respectively absorption disorder.

Known from the state of the art are various methods of measuring the intracranial pressure in the skull and of measuring parameters derived indirectly therefrom. For this purpose invasive methods are conventionally used in which a measuring probe is introduced through the skull into the brain tissue. Invasive methods have however various drawbacks, such as undesired bleeding, complicated execution of the method, locally limited measuring regions, etc.

Furthermore non-invasive measuring methods are used which are based e.g. on ultrasound and Doppler effect and use a correlation between an increased intracranial pressure and the pulsatility. However there exists a great variation in the pulsatility index, even in healthy people. In another method principles of fluid mechanics and neurophysiology are combined with results from magnetic resonance images, as described for example in "Noninvasive intracranial compliance and pressure based on dynamic magnetic resonance imaging of blood flow and cerebrospinal flow," Patricia B. Raksin et al., *Neurosurg. Focus*, Volume 14. Known from EP 0933061 B1 is a measuring configuration in which a proportionality between the intracranial pressure and a pressure existing in the external auditory canal is used for determining the intracranial pressure. Furthermore shown in US 2012/0136240 A1 is a system in which a controlled constriction of the jugular vein leads to a change in the blood outflow and the pressure of the blood outflow is measured, whereby the intracranial pressure is determined from the relationship between constriction and blood flow. Used thereby are e.g. near-infrared (NIR) sensors for determining the blood outflow. Furthermore absorption measuring methods in the near-infrared range are known for monitoring constituents of an organ, e.g. of the brain, in particular for monitoring oxygenated and deoxygenated blood, or for determining a concentration of oxygenated and deoxygenated blood e.g. in the brain, such as shown in U.S. Pat. No. 6,195,574 or 5,706,821.

A comparable situation is to be found with injuries and traumas of muscles that are tightly disposed in fascia, such as e.g. a lower leg or lower arm muscle. After a trauma, owing to compartmentally increased pressure inside a fascia, there exists a high risk that the muscle dies since blood circulation through the muscle is diminished by the pressure increase. The patients suffer a loss of muscles or even a life-threatening rhabdomyolysis syndrome. It is thus desirable to determine and to be able to monitor the pressure parameters in the muscles.

With the known methods, complicated algorithms and complex measurement configurations are required for determining pressure parameters in the body tissue. Moreover they are focused on specific parameters and are limited to few measurement sites, such as e.g. the ear. For measuring various parameters of a body tissue therefore different measuring systems must be used simultaneously or in succession. In addition, also the known non-invasive methods can be unpleasant and risky for the patient.

BRIEF SUMMARY

It is thus the object of the present invention to provide a measurement system and a method with which a simple and quick determination of parameters of a body tissue is possible, which get by with few system components, which can preferably measure a multiplicity of different parameters at the same time, and which make possible an application that is comfortable for a patient.

This object is achieved by the invention through a measurement system and a method as recited in the broadest claims herein. Advantageous embodiments and further embodiment examples are described in the dependent claims.

The present invention proposes a measurement system for measuring a parameter in a body tissue, which comprises at least one measurement device to be applied to the body of the body tissue, an optical unit for emission of light waves, at least one light guide between optical unit and measurement device for transmission of light waves and an analysis unit for analyzing measurement waves. The optical unit can preferably emit light waves of differing wavelength. At least one wavelength of the light waves lies in the absorption range of a body parameter of the body tissue. Light waves emitted from the optical unit are radiated, by means of the measurement device, into an optical measurement volume in the body tissue. Measurement waves received by the measurement device from the measurement volume are transmitted to the analysis unit. Thus the body parameter can be determined by means of determination of the light absorption of a wavelength in the measurement volume of the body tissue.

According to the invention, the analysis unit contains a transformation algorithm, which transforms the pulsatility of a body parameter, measured in the measurement volume, into a parameter of the pressure in the body tissue, whereby the body parameter is identified by determining the absorption of the light waves.

With the measurement system according to the invention it is thus possible to obtain a multiplicity of different parameters of a body tissue by means of a simple absorption measurement as it is essentially known. The measurement results of the absorption measurement for identification of a body parameter are further processed by the analysis unit, in that characteristic features of the pulsatility are determined. The ascertained pulsatility is assigned a pressure parameter by means of the transformation algorithm in accordance with the respective characteristic features, which pressure parameter indicates the pressure in the body tissue. Thus a pressure parameter of the body tissue can be determined without use of additional pressure measurement devices. Moreover determination of the pressure can take place at the same time with determination of other body parameters.

According to an example of the invention, the measurement system is designed for determination of at least one concentration parameter. The transformation algorithm transforms in this case the pulsatility of a concentration parameter of the body tissue, measured in the measurement volume, into the parameter of the pressure in the body tissue. Preferably identified by the measurement system in the measurement volume is a concentration of oxygenated hemoglobin, deoxygenated hemoglobin and/or an overall hemoglobin concentration. The pulsatility of this measured concentration is then transformed into the parameter of the pressure in the body tissue.

In an embodiment of the invention, the measurement system is designed to determine a body parameter in a measurement volume in the brain. By means of the transformation algorithm, a parameter of the intracranial pressure can be determined from the pulsatility of the body parameter in the brain measurement volume.

In another embodiment of the invention, the measurement system is designed for determining a body parameter in a measurement volume in a muscle. By means of the transformation algorithm a compartmental pressure parameter of the muscle can be determined from the pulsatility of the body parameter in the muscle measurement volume.

The invention is based on the surprising finding that various cerebral parameters can be deduced in a simple way from a combination of the teaching according to the Monro Kellie doctrine and the course of the pulsatility. In particular the intracranial pressure, the concentration of different brain constituents and the cerebral fluid volume can be identified. Furthermore metabolites and enzymes can also be identified. This finding can moreover be applied also to other organs. In particular it was also possible to develop a transformation algorithm for determination of a pressure parameter in the muscle. Furthermore the measurement system can also be used for determining parameters in bones.

The facts and circumstances on which the invention is based will be explained more closely with reference to the example of a measurement in the brain. In a first approach, the cranium can be assumed to be inelastic. Volume changes inside the skull due to the difference in blood flowing in and out are regularly within the range of 1 ml. All substances inside the cranium can be assumed to be incompressible. Furthermore a volume increase of a constituent of the brain, e.g. a tissue volume increase through a cerebral edema, can only be compensated by a compensatory reduction of another constituent, e.g. reduction of the cerebral fluid or of the blood volume. After these space reserves have been exhausted, there is an increase in the intracranial pressure. One speaks here of brain compliance. Although the intracranial pressure-volume relationship depends on such compensation mechanisms, it remains close to constant at least for an individual. Under pathological conditions, mass effects, such as a swelling of the brain, hemorrhage, tumor formation, etc., are more relevant, however, and, through the increase in volume, lead to the rise in the intracranial pressure. A pressure-volume curve is monoexponential and can be determined empirically in a known way.

On the other hand, the described pathological conditions have effects on the course of the pulsatility of the blood flow. With increased intracranial pressure, for example with a swelling of the brain, the heart must increasingly pump blood into the cranium against the intracranial pressure. At the same time, with constriction of the vessels, the speed of the blood in the vessels increases. The pulse wave of the blood flow induces in the cranium a volume change and thus influences the intracranial pressure and the compliance.

It has now been observed that, by means of the pressure-volume curve, the intracranial pressure can be deduced from the course, respectively from the change, of the amplitude of the pulsatility of a blood parameter. In particular the hemoglobin content in a brain segment and hence the intracranial pressure can be identified from the course of the amplitude of the blood pulsatility. Owing to the above-mentioned effects the ICP curve configuration and thus the morphology of the ICP curve changes.

According to the invention, by means of optical measuring methods, the course or respectively the change of e.g. concentration values for the various constituents of a body tissue are captured in the form of a measurement wave or respectively an optical measuring signal for tissue water, oxygenated hemoglobin, deoxygenated hemoglobin and preferably also for the overall hemoglobin value. The morphology of values of the pressure parameter, such as e.g. the intracranial pressure, is specified from a morphology of the measurement waves for the various constituents. From the thus obtained morphology of the intracranial pressure values the compliance and the mean intracranial pressure is determined.

The pulsatility of a body parameter is characterized e.g. by the peak within a pulse, as will be explained more precisely in the description of the figures. In general the amplitude decreases with increasing intracranial pressure, as soon as the compensation mechanisms are exhausted.

The pulsatility of the blood flow and thus the course, or respectively change, of its amplitude can be determined in a simple way by means of an optical measurement system according to the invention with a measurement device for non-invasive measurement of parameters of a body tissue. The measurement device thereby comprises an emitter-detector system, to be applied to an organ, such as e.g. the scalp or the skin over a muscle, which system is provided for emission and detection of the various light waves. Such a measurement device is described e.g. in the Swiss patent application of the applicant entitled "Messvorrichtung zur Bestimmung zerebraler Parameter" (Measuring device for determining cerebral parameters), No. 02266/12 of 6 Nov. 2012. Such a measurement device with a sensor unit and a sensor pad is provided for removable attachment of the measurement device to a body surface, such as e.g. the surface of the head, for instance the forehead. The information relating to features of this measurement device, as well as its advantages for carrying out measurements on the body tissue, in particular on brain tissue, is hereby incorporated in full into the description of the present invention. Referred to in particular is the information relating to optical measurements of parameters.

Furthermore, with the aid of such a measurement device, volumes inside the cranium can be determined and thereby absolute values can be determined for the concentration of water and hemoglobin in the brain tissue. Blood is composed of blood plasma (water, proteins, etc.) and corpuscular components, among them erythrocytes with hemoglobin. The concentration of the erythrocytes determines the hematocrit and thereby also the mass concentration of water in the blood. The cerebral blood volume is thereby determined by the relationship of mass of the brain to blood volume and by the relationship of hematocrit to the hemoglobin concentration in the brain. The intracranial volumes consist of volumes of white and gray brain matter, the blood volume and the cerebrospinal fluid (cerebral fluid). The same applies for a measurement on the muscle, the volume of the muscle being composed histologically of muscle cells with myofibrils. Chemically these contain about ¾ water and ¼ solid materials. The solid components are approximately 20% proteins, above all myosin, lipids, glycogen, creatine, etc.

The measurement system can determine a volume measurement value, which is made up of the intracranial volume and extracerebral parts, such as the cerebrospinal fluid volume, bone volume and skin volume.

According to the invention, the measurement device is preferably disposed with each measurement on the same measuring site of a patient, so that with each measurement the same optical volume segment is measured. The extracranial part, or respectively the external part in the case of the muscle, can thereby be seen as constant over time. It has now been shown that the concentration of a measured volume measured with the measurement system is representative for the whole cranium, or respectively muscle. In particular a volume measured with the measurement system in the near-infrared spectroscopy (NIRS) method is approximately representative for the entire cranium or respectively muscle. Thus with the measurement system an optical volume segment of the body tissue can be measured and from this the composition of the tissue portions in the entire brain or muscle can be deduced. The concentration change in the irradiated volume segment is thereby identified. The entire volume can be measured, if necessary, using known measuring methods such as e.g. CT methods. The transformation of the concentration values determined with the measurement device into volume values takes place by means of the analysis device, such as e.g. a computer, which is connected to the measurement device or to which the measurement values are able to be provided. The measurement values can be transmitted as optical signals, like the measurement waves received by the measurement device, or as electrical signals.

With a device and a method according to the present invention it is also possible in a simple, preferably non-invasive, way to carry out a determination of the tissue water. In so doing a multiplicity of light waves of differing wavelength are emitted from a light source of the measurement system and are conducted by the measurement device into the optical volume segment, the light waves lying preferably on the edge of the so-called bio-optical window. At least one wavelength lies in the range of the water absorption and is suitable and characteristic for the determination of the water concentration. By means of further wavelengths, oxygenated and deoxygenated blood as well as tissue material can be measured.

In general, different effects can be measured at the same time with a measurement system and a method according to the present invention. The spacing between the brain and skull, or respectively its change, can be identified through a transcranial measurement on the basis of an NIRS measurement. With increasing pressure, the reduction of the blood volume supplied can be measured, through the change, or respectively the course, of the amplitude of the pulsatility, as mentioned above. With the use of a multiplicity of different wavelengths, which penetrate essentially simultaneously an optical volume measurement segment of the body organ, such as e.g. the cranium, the concentration of different constituents, e.g. brain constituents, can be specified, for which their characteristic optical spectra are known. It is thereby advantageous if the weighting of the different absorptions is comparable, i.e. the product of absorption coefficient and of the concentration to be measured should be within the same order of magnitude for all constituents of the tissue to be measured. A representative measurement precision is thereby achieved.

In an embodiment, the optical measurement system has a measurement device for measuring an optical volume segment of the body tissue, which device is supplied by a light source with lights of a multiplicity of different wavelengths. The light source preferably provides light beams with at least four different wavelengths. At least one wavelength lies in the range of the water absorption. The other wavelengths are adapted to the other tissue constituents, e.g. brain constituents. For example, wavelengths between 750 nm and 1100 nm are used. The hemoglobin concentration and the concentration of white and gray matter can thereby be measured, for example. With a measurement of muscle, the wavelengths are preferably adapted to the absorption spectra of proteins and also of myoglobin. Proteins have, for example, optically measurable reactions at 200-300 nm, depending upon magnitude. Furthermore the different wavelengths are selected in such a way that the product of absorption coefficient and concentration lies within the same order of magnitude for all constituents to be measured. The measurement can take place essentially according to an NIRS method.

The measurement system further comprises an analysis device, in which e.g. a numerical method is implemented, which determines the concentration of the constituent in the tissue from the optical measurement by means of a linear equation system. Used for the equation system can be e.g. the generally known course of the pressure-volume curve of the cerebral or muscular pressure, which can be determined e.g. through a usual series of measurements. Or an average curve can be used as reference. From the change in the pulsatility along this curve the sought parameter, in particular the pressure, can be deduced. For this purpose, for example, the pulsatility can be determined at two different pressure or respectively volume values and can be extrapolated beyond these measurement values.

An increase or decrease of the cerebral fluid concentration can thus be derived from the determination of the concentration of the individual constituents in the brain tissue. In this way an increase or decrease of a cerebral edema can be determined, for example.

It is furthermore advantageous that, with at least one wavelength which reacts to changes in the blood concentration, the measurement system can measure a pulsatility of this parameter. For this purpose the above-mentioned measurement device identifies e.g. the light scattered or reflected in the measurement volume segment. The signal of the detected light beam, i.e. of the received measurement wave, is translated into the corresponding pulsatility of the measured parameter. The pulsatility is preferably determined based on a multiplicity of different wavelengths which react to changes in the blood concentration and a mean value formed from these data. With unchanging conditions, the amplitude of the pulsatility averaged over a multiplicity of pulse waves remains approximately the same. If the amplitude changes, this indicates a change in the pressure.

The measurement system according to the present invention can also be used with two or more measurement devices of the above-mentioned type, which each deliver measurement signals to the analysis unit. The measurement devices can be provided e.g. on opposite regions of the cranium or of a muscle. By means of a multiplicity of measurement devices different brain areas can be monitored, e.g. with respect to a differing cerebral fluid content or in general with respect to the composition of the tissue.

The measurement system can also comprise a marker device, by means of which a dye, preferably an indocyanine green (ICG) dye, is able to be introduced into the blood flow. The measurement system can then be used in an ICG-dye dilution mode, with which the blood volume in the tissue can be determined. This measurement is coupled with a continuously to-be-measured parameter, such as e.g. the total hemoglobin, whereby changes in the blood volume can be detected.

Alternatively to a non-invasive measurement device of the above-described type, the principle of the present invention can be advantageously implemented using a conventional probe, preferably a minimally invasive probe, e.g. in the form of an intracranial catheter. The identification of the desired parameter can take place according to the present invention by means of the received measurement signals of the probe.

The invention has been presented with reference to a multiplicity of embodiments. The individual technical features of one embodiment can absolutely be used also in combination with another embodiment, with the explained advantages. The description of the technical features according to the invention is thus not limited to the respective embodiment. In particular the features of a measurement on the cranium can be carried over to a measurement on a muscle or bone.

BRIEF DESCRIPTION OF THE FIGURES

An advantageous embodiment of the invention will be presented in the following with reference to the drawings, which serve merely purposes of explanation and are not to be interpreted in a limiting way. Features of the invention disclosed from the drawings should be viewed as belonging to the disclosure of the invention. In the drawings.

DETAILED DESCRIPTION OF VARIOUS EMBODIMENTS

Figure 1:
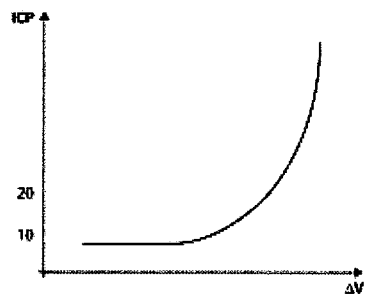
FIG. 1 is a pressure-volume curve of the intracranial pressure and of the intracranial volume.

Shown in FIG. 1 with reference to a pressure-volume curve is the relationship between the intracranial pressure and the intracranial volume. The pressure is thereby indicated in torr [mmHg] and the volume in units of a pressure change $\Delta V$. It can be seen therefrom that in a low range of the intracranial pressure up to approximately 10 mmHg an increase in volume does not bring about any substantial increase in pressure. In this range the compensation mechanisms are able to compensate for a volume change without the pressure rising. In a still normal range between 10 mmHg and 20 mmHg the intracranial pressure begins to climb with a volume increase. Starting with a pressure of 20 mmHg, which corresponds to a pathological pressure range, even a very slight increase in volume brings about a big increase in the intracranial pressure. This correlation between intracranial pressure and intracranial volume is used in the measurement system and method according to the present invention for determining cerebral parameters, as previously described.

Along this curve a pulsatility of blood values, such as e.g. the values of oxygenated or deoxygenated blood, show a change, or respectively a characteristic course. Thus through the determination of the pulsatility and the pressure-volume curve the intracranial pressure can be deduced.

Figure 2:
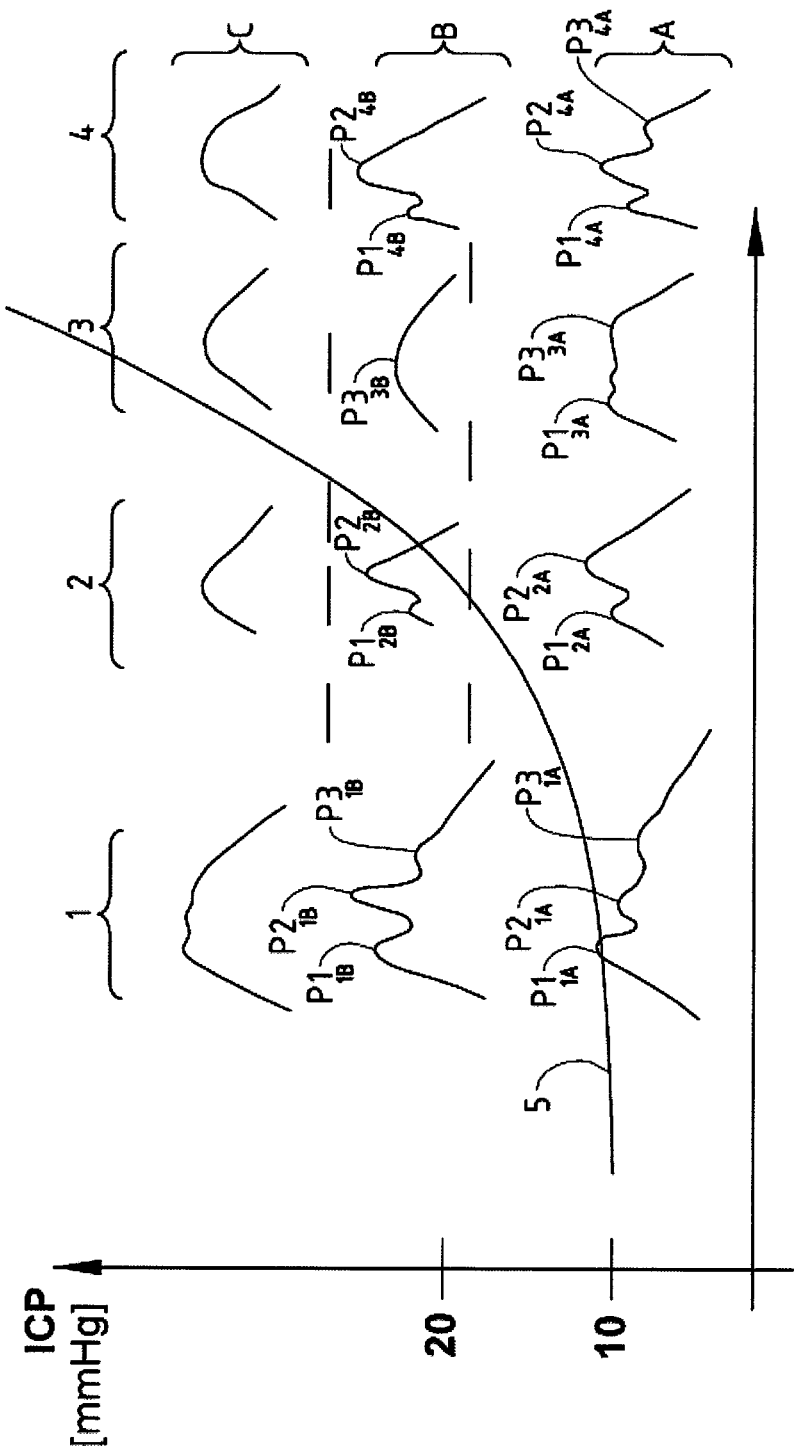
FIG. 2 is a diagrammatic overview of a correlation of different pulsatility results to parameters of the intracranial pressure.

Shown in FIG. 2, for an examination of the brain, is a diagrammatic overview of a correlation of different pulsatility results to parameters of the intracranial pressure. Shown on a vertical axis is again the intracranial pressure in torr [mmHg]. Shown in column 1 is the morphology of a pulse of an ICP measurement curve at three different values of the intracranial pressure. Shown in column 2 is the pulse course of a concentration of oxygenated hemoglobin ($Hb_{oxy}$), in column 3 the pulse course of a concentration of deoxygenated hemoglobin ($Hb_{deoxy}$), and in column 4 the pulse course of an overall hemoglobin concentration ($Hb_{tot}$), in each case with three different values of the intracranial pressure. The three different values of the intracranial pressure are separated in lines A, B and C. The pulse course in line A corresponds to an intracranial pressure of approximately 10 mmHg, in line B to an intracranial pressure of approximately 20 mmHg, and in line C to an intracranial pressure of significantly above 20 mmHg.

The course of the pulsatility of the intracranial pressure is known, and is described e.g. in "Intracranial Pressure Waveform Morphology and Intracranial Adaptive Capacity", *American Journal of Critical Care*, 2008; 17:545-554. Under normal conditions, as in the case of a pulse course in column 1, line A, the pulse course has three peaks. Peak $P1_{1A}$ comes from the pulsation of the choroid plexus (percussion wave) with a nearly constant amplitude. Peak $P2_{1A}$ comes from a rebound after the first arterial deflection (tidal wave) and varies in form and amplitude. Peak $P3_{1A}$ originates from a venous reaction after a dicrotic depression (dicrotic wave). Column 1, line B shows the pulse course of an ICP pulse with an increased ICP value compared with line A. Peak $P2_{1B}$ is clearly elevated, while peak $P1_{1B}$ remains substantially the same. Column 1, line C shows the pulse course of an ICP pulse in the pathological pressure range above 20 mmHg. The pulse course is flattened and shows only slightly formed peaks. In contrast to the present invention, the above-mentioned publication states that the peaks of the pulse course of the intracranial pressure are not any clinically relevant factor and are not suitable for determining a condition of a patient.

Figure 3:
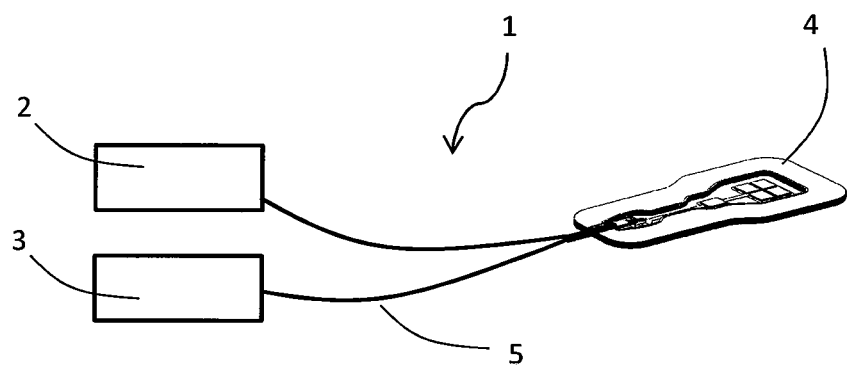
FIG. 3 is a schematic representation of a measuring system according to the present invention.

The pulse course of a concentration of oxygenated hemoglobin, deoxygenated hemoglobin and an overall hemoglobin concentration was determined by means of a measurement device according to FIG. 3 through NIRS measurement. The pulse course of the concentration of $Hb_{oxy}$ under normal conditions is shown in column 2, line A. Peak $P1_{2A}$ shows an amplitude of the choroid plexus, and peak $P2_{2A}$ an amplitude of an arterial component of the pulse. The arterial component clearly rises with increasing intracranial pressure, as can be seen in column 2, line B, from the elevation of the peak $P2_{2B}$. The pulse course of the concentration of $Hb_{deoxy}$ under normal conditions is shown in column 3, line A. Peak $P1_{3A}$ shows again the amplitude of the choroid plexus. The arterial component of the pulse is hardly visible, whereas the venous component strongly influences the pulse course with a peak $P3_{3A}$. With elevated pressure the venous component dominates the pulse course with peak $P3_{3B}$, as can be seen in column 3, line B. The pulse course of the overall hemoglobin concentration in the normal pressure range has clearly pronounced peaks $P1_{4A}$, $P2_{4A}$ and $P3_{4A}$, see column 4, line A. With elevated pressure the venous component disappears and the arterial component is more pronounced with peak $P2_{4B}$. In the pathological pressure range above 20 mmHg the pulse course shows no individual peaks anymore; instead the pulse is identified by a pulse over the width of a single peak value.

Measurements have shown that the course of the pulsatility of the body parameter, such as the concentration here, determined through absorption measurement by means of the measurement device, is reproducible and can be clearly related to the values of the intracranial pressure. Basically one body parameter is sufficient for this purpose, such as e.g. oxygenated hemoglobin. The use of a plurality of body parameters, e.g. $Hb_{oxy}$, $Hb_{deoxy}$ and $Hb_{tot}$, can increase the measurement precision however. The transformation algorithm of the measurement system comprises for this purpose a comparison algorithm, with which the measured pulsatility course can be assigned a specific pressure value. For this purpose reference curves for the course of the intracranial pressure can be made use of. Above and beyond this, the pulsatility of the individual concentrations can be assigned to an intracranial pressure by means of the pressure-volume curve of FIG. 1. Also a combination with a comparison with the peaks of the intracranial pressure is possible in order to determine the existing pressure.

Advantageous with the invention is that the determination of body parameters can be used that are able to be detected in a simple way and which are by themselves helpful for the monitoring of a patient. It is not necessary to use an additional measuring unit for the determination of the pressure.

Shown schematically in FIG. 3 is a measurement system 1 for measuring at least one body parameter according to the invention. The measurement system comprises at least one measurement device 4, a light-emitting optical unit 3 and an analysis unit 2. The measurement device is designed as non-invasive patch, which is provided on a body organ, such as e.g. a cranium or on a muscle, over an optical measurement volume in the body tissue. Further provided are light guides 5 between optical unit 3, measurement device 4 and analysis unit 2 for transmission of light waves. Light waves emitted from the optical unit 3 are thereby radiated by means of the measurement device 4 into the optical measurement volume in the brain, and measurement waves received by the measurement device 4 from the brain are transmitted to the analysis unit 2. The optical unit 3 provides a multiplicity of light waves of different wavelength to the at least one measurement device 4. Preferably at least one wavelength thereby lies in the range of the water absorption and each further wavelength is selected according to the absorption of one of the body parameters to be determined.

At least four light waves of differing wavelength are preferably provided, the weighting of the different absorptions of the wavelengths in the optical measurement volume lying within an order of magnitude. For measurement of each constituent in the body tissue, a wavelength corresponding to the absorption of this constituent is preferably provided. Preferably provided are a wavelength corresponding to the absorption for measuring a concentration of body tissue, a further wavelength corresponding to the absorption for measuring a concentration of deoxygenated blood and, if desired, still another wavelength corresponding to the absorption for measuring a concentration of oxygenated blood. The light waves and the measurement waves for all parameters to be measured can be conducted simultaneously by the measurement device.

In the corresponding wavelengths, which react to changes in the blood concentration, the system can measure the pulsatility of the measurement value. With unchanging conditions the amplitude of the pulsatility averaged over a multiplicity of pulse waves should remain approximately the same. If the amplitude changes, this indicates a change in the pressure in the body tissue. A rise or respectively a drop in the pressure is clearly determined from the measured values, by means of a corresponding correlation in the analysis unit. An increase or decrease in the tissue water concentration is detected from the determination of the concentration of the constituents in the body tissue. An increase or decrease of an edema can thereby be diagnosed. The hemodynamics, the concentration of the tissue components, the magnitude of the edema and of the pressure are preferably determined at the same time using the measurement system.

One example for implementation of the measuring system according to the invention is the examination of the brain and the determination of the intracranial pressure, or respectively its change, as explained in the preceding. The measurement system and the method are also suitable for examination of muscle tissue in order to determine the pressure in a muscle compartment or respectively its change. Various embodiments will now be further described for purposes of a complete disclosure; it should be understood, of course, that such description is non-limiting and exemplary, such that still further modifications to or variations thereof may be possible without departing from the scope or nature of the present invention.

With that context, the present invention proposes a measurement system for measuring a parameter in a body tissue, which comprises at least one measurement device to be applied to the body of the body tissue, an optical unit for emission of light waves, at least one light guide between optical unit and measurement device for transmission of light waves and an analysis unit for analyzing measurement waves. The optical unit can preferably emit light waves of differing wavelength. At least one wavelength of the light waves lies in the absorption range of a body parameter of the body tissue. Light waves emitted from the optical unit are radiated, by means of the measurement device, into an optical measurement volume in the body tissue. Measurement waves received by the measurement device from the measurement volume are transmitted to the analysis unit. Thus the body parameter can be determined by means of determination of the light absorption of a wavelength in the measurement volume of the body tissue.

According to the invention, the analysis unit contains a transformation algorithm, which transforms the pulsatility of a body parameter, measured in the measurement volume, into a parameter of the pressure in the body tissue, whereby the body parameter is identified by determining the absorption of the light waves.

With the measurement system according to the invention it is thus possible to obtain a multiplicity of different parameters of a body tissue by means of a simple absorption measurement as it is essentially known. The measurement results of the absorption measurement for identification of a body parameter are further processed by the analysis unit, in that characteristic features of the pulsatility are determined. The ascertained pulsatility is assigned a pressure parameter by means of the transformation algorithm in accordance with the respective characteristic features, which pressure parameter indicates the pressure in the body tissue. Thus a pressure parameter of the body tissue can be determined without use of additional pressure measurement devices. Moreover determination of the pressure can take place at the same time with determination of other body parameters.

According to an example of the invention, the measurement system is designed for determination of at least one concentration parameter. The transformation algorithm transforms in this case the pulsatility of a concentration parameter of the body tissue, measured in the measurement volume, into the parameter of the pressure in the body tissue. Preferably identified by the measurement system in the measurement volume is a concentration of oxygenated hemoglobin, deoxygenated hemoglobin and/or an overall hemoglobin concentration. The pulsatility of this measured concentration is then transformed into the parameter of the pressure in the body tissue.

In an embodiment of the invention, the measurement system is designed to determine a body parameter in a measurement volume in the brain. By means of the transformation algorithm, a parameter of the intracranial pressure can be determined from the pulsatility of the body parameter in the brain measurement volume.

In another embodiment of the invention, the measurement system is designed for determining a body parameter in a measurement volume in a muscle. By means of the transformation algorithm a compartmental pressure parameter of the muscle can be determined from the pulsatility of the body parameter in the muscle measurement volume.

The invention is based on the surprising finding that various cerebral parameters can be deduced in a simple way from a combination of the teaching according to the Monro Kellie doctrine and the course of the pulsatility. In particular the intracranial pressure, the concentration of different brain constituents and the cerebral fluid volume can be identified. Furthermore metabolites and enzymes can also be identified. This finding can moreover be applied also to other organs. In particular it was also possible to develop a transformation algorithm for determination of a pressure parameter in the muscle. Furthermore the measurement system can also be used for determining parameters in bones.

The facts and circumstances on which the invention is based will be explained more closely with reference to the example of a measurement in the brain. In a first approach, the cranium can be assumed to be inelastic. Volume changes inside the skull due to the difference in blood flowing in and out are regularly within the range of 1 ml. All substances inside the cranium can be assumed to be incompressible. Furthermore a volume increase of a constituent of the brain, e.g. a tissue volume increase through a cerebral edema, can only be compensated by a compensatory reduction of another constituent, e.g. reduction of the cerebral fluid or of the blood volume. After these space reserves have been exhausted, there is an increase in the intracranial pressure. One speaks here of brain compliance. Although the intracranial pressure-volume relationship depends on such compensation mechanisms, it remains close to constant at least for an individual. Under pathological conditions, mass effects, such as a swelling of the brain, hemorrhage, tumor formation, etc., are more relevant, however, and, through the increase in volume, lead to the rise in the intracranial pressure. A pressure-volume curve is monoexponential and can be determined empirically in a known way.

On the other hand, the described pathological conditions have effects on the course of the pulsatility of the blood flow. With increased intracranial pressure, for example with a swelling of the brain, the heart must increasingly pump blood into the cranium against the intracranial pressure. At the same time, with constriction of the vessels, the speed of the blood in the vessels increases. The pulse wave of the blood flow induces in the cranium a volume change and thus influences the intracranial pressure and the compliance.

It has now been observed that, by means of the pressure-volume curve, the intracranial pressure can be deduced from the course, respectively from the change, of the amplitude of the pulsatility of a blood parameter. In particular the hemoglobin content in a brain segment and hence the intracranial pressure can be identified from the course of the amplitude of the blood pulsatility. Owing to the above-mentioned effects the ICP curve configuration and thus the morphology of the ICP curve changes.

According to the invention, by means of optical measuring methods, the course or respectively the change of e.g. concentration values for the various constituents of a body tissue are captured in the form of a measurement wave or respectively an optical measuring signal for tissue water, oxygenated hemoglobin, deoxygenated hemoglobin and preferably also for the overall hemoglobin value. The morphology of values of the pressure parameter, such as e.g. the intracranial pressure, is specified from a morphology of the measurement waves for the various constituents. From the thus obtained morphology of the intracranial pressure values the compliance and the mean intracranial pressure is determined.

The pulsatility of a body parameter is characterized e.g. by the peak within a pulse, as will be explained more precisely in the description of the figures. In general the amplitude decreases with increasing intracranial pressure, as soon as the compensation mechanisms are exhausted.

The pulsatility of the blood flow and thus the course, or respectively change, of its amplitude can be determined in a simple way by means of an optical measurement system according to the invention with a measurement device for non-invasive measurement of parameters of a body tissue. The measurement device thereby comprises an emitter-detector system, to be applied to an organ, such as e.g. the scalp or the skin over a muscle, which system is provided for emission and detection of the various light waves. Such a measurement device is described e.g. in the Swiss patent application of the applicant entitled "Messvorrichtung zur Bestimmung zerebraler Parameter" (Measuring device for determining cerebral parameters), No. 02266/12 of 6 Nov. 2012. Such a measurement device with a sensor unit and a sensor pad is provided for removable attachment of the measurement device to a body surface, such as e.g. the surface of the head, for instance the forehead. The information relating to features of this measurement device, as well as its advantages for carrying out measurements on the body tissue, in particular on brain tissue, is hereby incorporated in full into the description of the present invention. Referred to in particular is the information relating to optical measurements of parameters.

Furthermore, with the aid of such a measurement device, volumes inside the cranium can be determined and thereby absolute values can be determined for the concentration of water and hemoglobin in the brain tissue. Blood is composed of blood plasma (water, proteins, etc.) and corpuscular components, among them erythrocytes with hemoglobin. The concentration of the erythrocytes determines the hematocrit and thereby also the mass concentration of water in the blood. The cerebral blood volume is thereby determined by the relationship of mass of the brain to blood volume and by the relationship of hematocrit to the hemoglobin concentration in the brain. The intracranial volumes consist of volumes of white and gray brain matter, the blood volume and the cerebrospinal fluid (cerebral fluid). The same applies for a measurement on the muscle, the volume of the muscle being composed histologically of muscle cells with myofibrils. Chemically these contain about ¾ water and ¼ solid materials. The solid components are approximately 20% proteins, above all myosin, lipids, glycogen, creatine, etc.

The measurement system can determine a volume measurement value, which is made up of the intracranial volume and extracerebral parts, such as the cerebrospinal fluid volume, bone volume and skin volume.

According to the invention, the measurement device is preferably disposed with each measurement on the same measuring site of a patient, so that with each measurement the same optical volume segment is measured. The extracranial part, or respectively the external part in the case of the muscle, can thereby be seen as constant over time. It has now been shown that the concentration of a measured volume measured with the measurement system is representative for the whole cranium, or respectively muscle. In particular a volume measured with the measurement system in the near-infrared spectroscopy (NIRS) method is approximately representative for the entire cranium or respectively muscle. Thus with the measurement system an optical volume segment of the body tissue can be measured and from this the composition of the tissue portions in the entire brain or muscle can be deduced. The concentration change in the irradiated volume segment is thereby identified. The entire volume can be measured, if necessary, using known measuring methods such as e.g. CT methods. The transformation of the concentration values determined with the measurement device into volume values takes place by means of the analysis device, such as e.g. a computer, which is connected to the measurement device or to which the measurement values are able to be provided. The measurement values can be transmitted as optical signals, like the measurement waves received by the measurement device, or as electrical signals.

With a device and a method according to the present invention it is also possible in a simple, preferably non-invasive, way to carry out a determination of the tissue water. In so doing a multiplicity of light waves of differing wavelength are emitted from a light source of the measurement system and are conducted by the measurement device into the optical volume segment, the light waves lying preferably on the edge of the so-called bio-optical window. At least one wavelength lies in the range of the water absorption and is suitable and characteristic for the determination of the water concentration. By means of further wavelengths, oxygenated and deoxygenated blood as well as tissue material can be measured.

In general, different effects can be measured at the same time with a measurement system and a method according to the present invention. The spacing between the brain and skull, or respectively its change, can be identified through a transcranial measurement on the basis of an NIRS measurement. With increasing pressure, the reduction of the blood volume supplied can be measured, through the change, or respectively the course, of the amplitude of the pulsatility, as mentioned above. With the use of a multiplicity of different wavelengths, which penetrate essentially simultaneously an optical volume measurement segment of the body organ, such as e.g. the cranium, the concentration of different constituents, e.g. brain constituents, can be specified, for which their characteristic optical spectra are known. It is thereby advantageous if the weighting of the different absorptions is comparable, i.e. the product of absorption coefficient and of the concentration to be measured should be within the same order of magnitude for all constituents of the tissue to be measured. A representative measurement precision is thereby achieved.

In an embodiment, the optical measurement system has a measurement device for measuring an optical volume segment of the body tissue, which device is supplied by a light source with lights of a multiplicity of different wavelengths. The light source preferably provides light beams with at least four different wavelengths. At least one wavelength lies in the range of the water absorption. The other wavelengths are adapted to the other tissue constituents, e.g. brain constituents. For example, wavelengths between 750 nm and 1100 nm are used. The hemoglobin concentration and the concentration of white and gray matter can thereby be measured, for example. With a measurement of muscle, the wavelengths are preferably adapted to the absorption spectra of proteins and also of myoglobin. Proteins have, for example, optically measurable reactions at 200-300 nm, depending upon magnitude. Furthermore the different wavelengths are selected in such a way that the product of absorption coefficient and concentration lies within the same order of magnitude for all constituents to be measured. The measurement can take place essentially according to an NIRS method.

The measurement system further comprises an analysis device, in which e.g. a numerical method is implemented, which determines the concentration of the constituent in the tissue from the optical measurement by means of a linear equation system. Used for the equation system can be e.g. the generally known course of the pressure-volume curve of the cerebral or muscular pressure, which can be determined e.g. through a usual series of measurements. Or an average curve can be used as reference. From the change in the pulsatility along this curve the sought parameter, in particular the pressure, can be deduced. For this purpose, for example, the pulsatility can be determined at two different pressure or respectively volume values and can be extrapolated beyond these measurement values.

An increase or decrease of the cerebral fluid concentration can thus be derived from the determination of the concentration of the individual constituents in the brain tissue. In this way an increase or decrease of a cerebral edema can be determined, for example.

It is furthermore advantageous that, with at least one wavelength which reacts to changes in the blood concentration, the measurement system can measure a pulsatility of this parameter. For this purpose the above-mentioned measurement device identifies e.g. the light scattered or reflected in the measurement volume segment. The signal of the detected light beam, i.e. of the received measurement wave, is translated into the corresponding pulsatility of the measured parameter. The pulsatility is preferably determined based on a multiplicity of different wavelengths which react to changes in the blood concentration and a mean value formed from these data. With unchanging conditions, the amplitude of the pulsatility averaged over a multiplicity of pulse waves remains approximately the same. If the amplitude changes, this indicates a change in the pressure.

The measurement system according to the present invention can also be used with two or more measurement devices of the above-mentioned type, which each deliver measurement signals to the analysis unit. The measurement devices can be provided e.g. on opposite regions of the cranium or of a muscle. By means of a multiplicity of measurement devices different brain areas can be monitored, e.g. with respect to a differing cerebral fluid content or in general with respect to the composition of the tissue.

The measurement system can also comprise a marker device, by means of which a dye, preferably an indocyanine green (ICG) dye, is able to be introduced into the blood flow. The measurement system can then be used in an ICG-dye dilution mode, with which the blood volume in the tissue can be determined. This measurement is coupled with a continuously to-be-measured parameter, such as e.g. the total hemoglobin, whereby changes in the blood volume can be detected.

Alternatively to a non-invasive measurement device of the above-described type, the principle of the present invention can be advantageously implemented using a conventional probe, preferably a minimally invasive probe, e.g. in the form of an intracranial catheter. The identification of the desired parameter can take place according to the present invention by means of the received measurement signals of the probe.

The invention claimed is:

1. A measurement system for measuring at least one parameter in a body tissue, said system comprising:
   at least one measurement device for measuring an optical volume segment of the body tissue, the at least one measurement device being configured to be applied to the body tissue;
   an optical unit configured for emitting at least four light waves having differing wavelengths, at least one wavelength of the emitted at least four light waves being in a range of absorption of the at least one parameter in the body tissue;
   at least one light guide located between the optical unit and the at least one measurement device, the at least one light guide being configured for transmission of the at least four light waves with differing wavelengths; and
   an analysis unit configured for analyzing measurement wave signals received from a detector of the measurement device,
   wherein:
       the at least four light waves with differing wavelengths emitted by the optical unit are radiated into the optical volume segment of the body tissue via the at least one measurement device;
       the measurement wave signals from the optical volume segment of the body tissue, detected by the detector, are transmitted to and received by the analysis unit;
       the analysis unit comprises a transformation algorithm, the transformation algorithm processing the measurement wave signals to determine a morphology for a set of measurement wave signals for at least one parameter indicative of intensity related to absorption wavelength, determining changes of concentration values of the at least one parameter, and transforming the morphology of the set of measurement wave signals into a parameter indicative of a pressure in the body tissue;
       the transformation algorithm identifies the pressure in the body tissue through an operation of comparison between a pressure reference course and at least one of the measurement wave signals or a peak of the measurement wave signals of the at least one parameter in the body tissue.

2. The measurement system according to claim 1, wherein the parameter indicative of the pressure in the body tissue is based further upon a concentration value of the at least one parameter.

3. The measurement system according to claim 2, wherein the parameter indicative of the pressure in the body tissue is based further upon at least one of a concentration of oxygenated hemoglobin, deoxygenated hemoglobin or an overall hemoglobin concentration, measured in the optical volume segment.

4. The measurement system according to claim 1, wherein the parameter is a parameter of intracranial pressure in a brain.

5. The measurement system according to claim 1, wherein the parameter is a compartmental pressure parameter of a muscle.

6. The measurement system according to claim 1, wherein one of the at least four wavelengths is selected to lie in the range of the absorption of water, and other of the at least four wavelengths are selected to lie in the range of the absorption of the at least one parameter of the body tissue to be determined.

7. The measurement system according to claim 1, wherein:
   the at least four wavelengths are selected such that for each parameter in the body tissue to be measured a constituent is identified, and
   a product of an absorption coefficient and a concentration of the constituent to be measured for each of the wavelengths lies within an order of magnitude.

8. The measurement system according to claim 1, wherein:
   for different parameters in the body tissue to be measured different constituents are identified; and
   a set of wavelengths is provided according to absorption of a set of the different constituents for measurement of concentration of the different constituents.

9. The measurement system according to claim 1, wherein a multiplicity of emitted light waves and a multiplicity of received measurement wave signals are conducted simultaneously in the at least one measurement device.

10. The measurement system according to claim 1, wherein the at least one measurement device is provided as a non-invasive measurement device.

11. The measurement system according to claim 1, wherein implemented in the analysis unit is a numerical method which identifies, by means of a linear equation system, at least one of: a tissue water volume, a concentration of blood, or a concentration of a parameter in the body tissue.

12. The measurement system according to claim 1, wherein a marker device is provided for introduction of a dye into a blood flow of the body tissue and the measurement system comprises a mode for determination of a dye concentration in the blood flow.

13. A method for measuring the at least one parameter in a body tissue, the method comprising:
    providing the measurement system according to claim 1,
    emitting, via the optical unit, the at least four light waves having differing wavelengths,
    transmitting, via the at least one light guide and to the measurement device, the at least four light waves with differing wavelengths,
    receiving, from the detector and at the analysis unit, measurement wave signals, and
    deducing, via the transformation algorithm, the pressure in the body tissue.

14. The method for measuring at least one parameter according to claim 13, further comprising the step of simultaneously determining a hemodynamics and a concentration of constituents of the brain or a muscle, using the numerical method, from the measurement wave signals of a multiplicity of light waves of differing wavelengths.

15. The measurement system according to claim 1, wherein for a set of constituents in the body tissue a corresponding set of wavelengths is provided according to absorption of the set of constituents for measurement of at least one of: concentration values of the set of constituents in the body tissue or a wavelength according to absorption for measurement of a concentration of blood.

16. The measurement system according to claim 1, wherein a difference of the morphology of the set of measurement wave signals is a difference among amplitudes of peaks of the measurement wave signals identifying difference of the concentration of the parameter in the body tissue with the at least four light waves of differing wavelengths.

17. The measurement system according to claim 1, wherein a difference of the morphology of the set of measurement wave signals is a difference among waveforms of the measurement wave signals identifying difference of the concentration of the parameter in the body tissue with the at least four light waves of differing wavelengths.

* * * * *